United States Patent [19]

Arseneau

[11] 3,984,689
[45] Oct. 5, 1976

[54] SCINTILLATION CAMERA FOR HIGH ACTIVITY SOURCES
[75] Inventor: Roger E. Arseneau, Arlington Heights, Ill.
[73] Assignee: G. D. Searle & Co., Skokie, Ill.
[22] Filed: Nov. 27, 1974
[21] Appl. No.: 527,547

[52] U.S. Cl. ............................ 250/369; 250/363 S
[51] Int. Cl.² ........................................ G01T 1/164
[58] Field of Search ......... 250/363, 366, 369, 363 S

[56] References Cited
UNITED STATES PATENTS

| 3,011,057 | 11/1961 | Anger | 250/366 |
|---|---|---|---|
| 3,732,419 | 5/1973 | Kulberg et al. | 250/366 |
| 3,732,420 | 5/1973 | Brunnett et al. | 250/252 |
| 3,793,520 | 2/1974 | Grenier | 250/366 |

Primary Examiner—Archie R. Borchelt
Attorney, Agent, or Firm—Walter C. Ramm; Peter J. Sgarbossa; Albert Tockman

[57] ABSTRACT

A scintillation camera is provided with electrical components which expand the intrinsic maximum rate of acceptance for processing of pulses emanating from detected radioactive events. Buffer storage is provided to accommodate temporary increases in the level of radioactivity. An early provisional determination of acceptability of pulses allows many unacceptable pulses to be discarded at an early stage.

14 Claims, 13 Drawing Figures

SCINTILLATION CAMERA FOR HIGH ACTIVITY SOURCES

The present invention relates to an improvement in a scintillation camera used for clinical medical diagnosis. Advanced recognition of many unacceptable pulses allows the scintillation camera to discard such pulses at an early stage in processing. This frees the camera to process a greater number of pulses of interest within a given period of time. Temporary buffer storage allows the scintillation camera to accommodate pulses received at a rate in excess of its maximum rated capability due to statistical fluctuations in the level of radioactivity of the radiation source measured.

BACKGROUND OF THE INVENTION

Scintillation cameras have, for several years, been used regularly as a clinical tool in diagnosing biological abnormalities. Tumors, lesions, and clotting can be readily located in many parts of the body of a patient being studied using a scintillation camera. U.S. Pat. No. 3,011,057 describes in detail the operation and function of a scintillation camera as envisioned by its inventor, Hal O. Anger. Use of a scintillation camera has rapidly expanded, as applications of the device were developed.

There have heretofore remained, however, certain limitation in connection with the use of a scintillation camera. A scintillation camera employs an array of photodetectors viewing overlapping portions of a scintillation crystal, usually formed of thallium-activated sodium iodide. The photodetectors produce electrical pulses in response to discrete quanta of radiation impinging upon the scintillation crystal. These pulses are processed by position computation circuitry, which registers the relative locations of quanta of radiation detected by the crystal for that radiation which lies within a specific energy range of interest. The position computation circuitry has heretofore been constructed so that processing of pulses emanating from different detected radioactive events have necessarily been performed sequentially. That is, pulses could be accepted and processed from only one quanta of radiation at a time. Since the processing of pulses requires a finite interval of time, any new pulses generated during such a finite interval are lost, since the computational circuitry is unable to accept them. Thus, information from a portion of radioactive events occurring is irretrievably lost. In many instances, compensation for the resulting lost information has heretofore been effected by merely extending the duration of the clinical study. However, the information lost increases as a percentage of total radiation received with an increase in the rate at which quanta of radiation are detected by the scintillation crystal. That is, the percentage of information lost increases with level of radioactivity. At count rates above about 100,000 counts per second, conventional camera systems become oversaturated and fail to perform. The finite interval of time during which the position computation circuitry is unavailable for processing pulses from new radioactive events is called "dead time". This dead time is the same for all detected radioactive events in conventional commercial scintillation cameras, and is of the order of about 2.5 microseconds per detected event. This average dead time can be markedly reduced employing the combination of components of the present invention. This reduction in average dead time is achieved by accomplishing several objectives of the present invention.

One objective of the invention is to reduce the average dead time of a scintillation camera by prematurely terminating processing of those pulses which will eventually be rejected anyway. To this end, a preliminary differential discriminator is provided to reject at an early stage those pulses which clearly will eventually be found to be unacceptable for tabulation. Having thus reduced the dead time associated with clearly unacceptable pulses, intrinsic maximum rate of acceptance by the scintillation camera of pulses for processing is increased.

Another objective of the invention is to accommodate increases in radioactivity rate due to statistical variations in the number of quanta of radiation detected by the scintillation crystal. Accommodation of such increases without a loss in camera response sensitivity is achieved by providing a plurality of stages of buffer storage for electrical pulses produced in response to detected radiation. The position computation circuitry of the camera is thereby operative to accommodate statistical fluctuations in the rate at which pulses are received for processing, even when the nominal level of radiation received has reached the intrinsic maximum rate of acceptance of pulses for processing.

A further objective is to provide a means for detection and expulsion of pulses in the position computation circuitry which are generated in response to the detection of different quanta of radiation. Expulsion is carried out at an early stage in pulse processing to reduce the dead time in the circuitry attributable to the concurrent existence of such electrical pulses, the concurrent existence thereof being referred to as "pulse pile-up". Pulse pile-up is when a second pulse occurs before the first pulse has decayed. The second pulse occurs during the integrating time of the first pulse.

Another object of the invention is to prevent pulse distortion at high levels of radioactivity due to base line shift of capacitively coupled circuits by using DC coupling through all circuits. Pulse distortion is minimized by DC coupling of the photodetector amplifiers, by running the anodes of the photodetectors at ground potential and connecting the photocathodes thereof to a negative high voltage source. Direct coupling of the anodes to the amplifiers prevents the build-up of a base line voltage, especially when the system is processing a large number of pulses. Such a base line voltage results in distortion of pulses during shaping and integration, thereby contributing to decreased accuracy to pulses of interest. By employing the present invention, pulse amplitude distortion is alleviated and a greater number of pulses of interest and a fewer number of extraneous pulses are processed and registered.

Sensitivity to the energy range of interest is further improved by the provision of a means for automatic peak adjustment of the discriminator levels of the scintillation camera. A pulse energy peak of interest can thereby be tuned in better at the center of a pulse energy window. Adjustment of the window width is made in equal increments on either side of the center of the peak, rather than in one direction only from a single base line discriminator level.

BRIEF DESCRIPTION OF THE INVENTION

In a broad aspect, this invention is in a scintillation camera employing an array of photodetectors viewing overlapping portions of a scintillation crystal and producing electrical pulses in response to quanta of radiation impinging upon such scintillation crystal, and position computation circuitry for processing said pulses to register the relative locations of quanta of radiation detected by said crystal within a specific energy range of interest, wherein said position computation circuitry includes electrical components defining an intrinsic maximum rate of acceptance of said pulses for processing, the improvement comprising means for increasing the intrinsic maximum rate of acceptance of said pulses for processing.

The invention is further illustrated with reference to the accompanying drawings in which FIG. 1 is an elevational view of a scintillation camera with which the present invention may be employed, FIG. 2A is a diagram in partial schematic form depicting the arrangement of electrical components according to this invention, FIG. 2B is a continuation of FIG. 2A arranged for positioning to the right hand side thereof, FIG. 2C is a continuation of FIG. 2B arranged for positioning to the right hand side thereof, FIG. 3A is a detailed diagram of the high voltage connections to a photodetector in a conventional scintillation camera, FIG. 3B is a detailed diagram of the high voltage connections to photodetector PM1 in FIG. 2A, FIG. 4A depicts the voltage output at point C in FIG. 3A, FIG. 4B depicts the voltage output at point C in FIG. 3B, FIG. 5 depicts the function of the preliminary differential discriminator of the present invention, FIG. 5A depicts a plurality of energy bands within which pulses are rejected by a modified preliminary differential discriminator.

FIG. 6 depicts the function of the operation of the pile-up control circuit 15 in FIG. 2B, FIG. 6A depicts integrator charging of prior art systems as contained with those of the present invention, FIG. 7 is a detailed diagram in partial schematic form further illustrating the analyzer 21 in FIG. 2B.

DETAILED DESCRIPTION OF THE INVENTION

Figure 1:
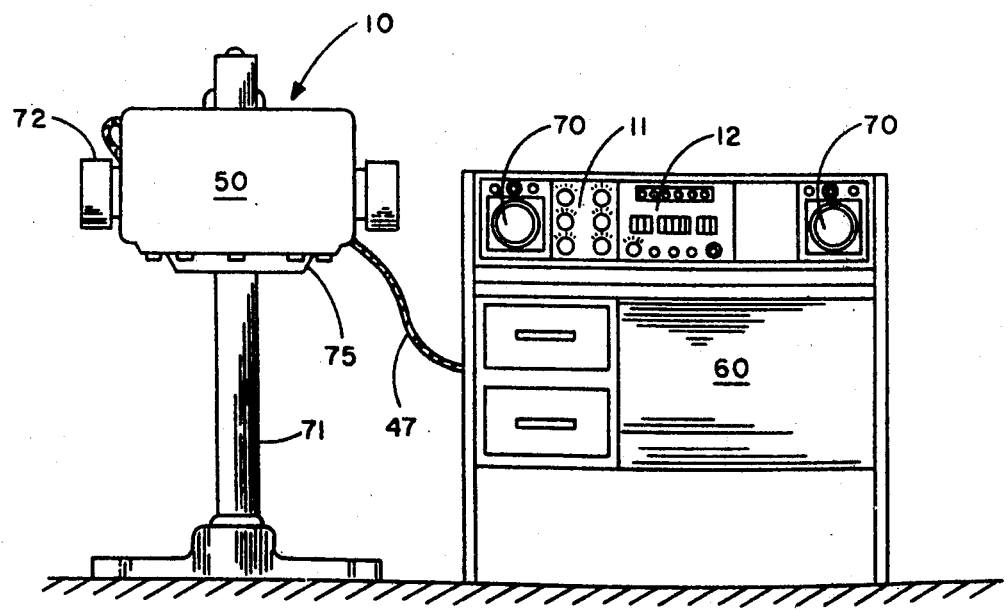
Figure 2A:
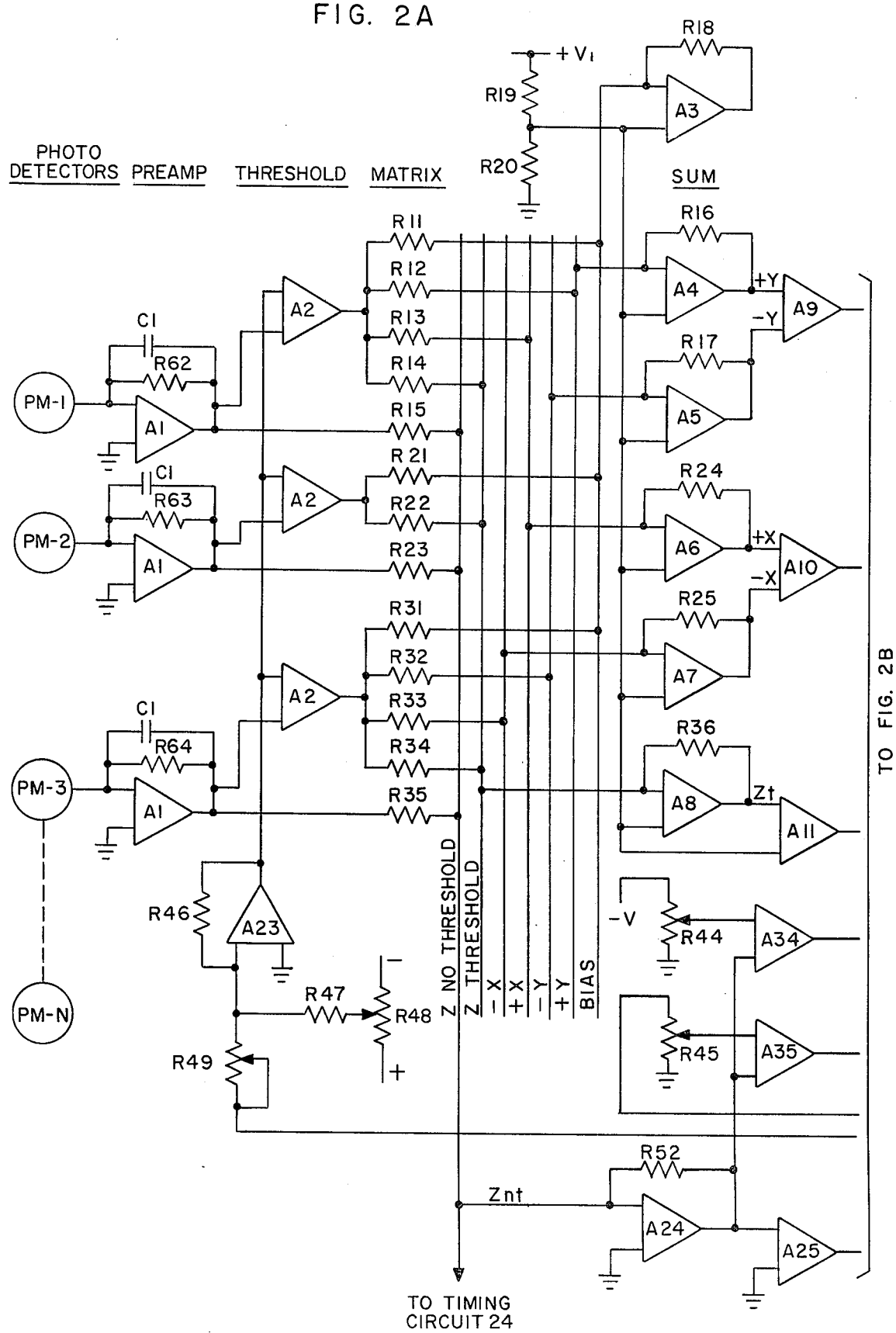
Figure 2B:
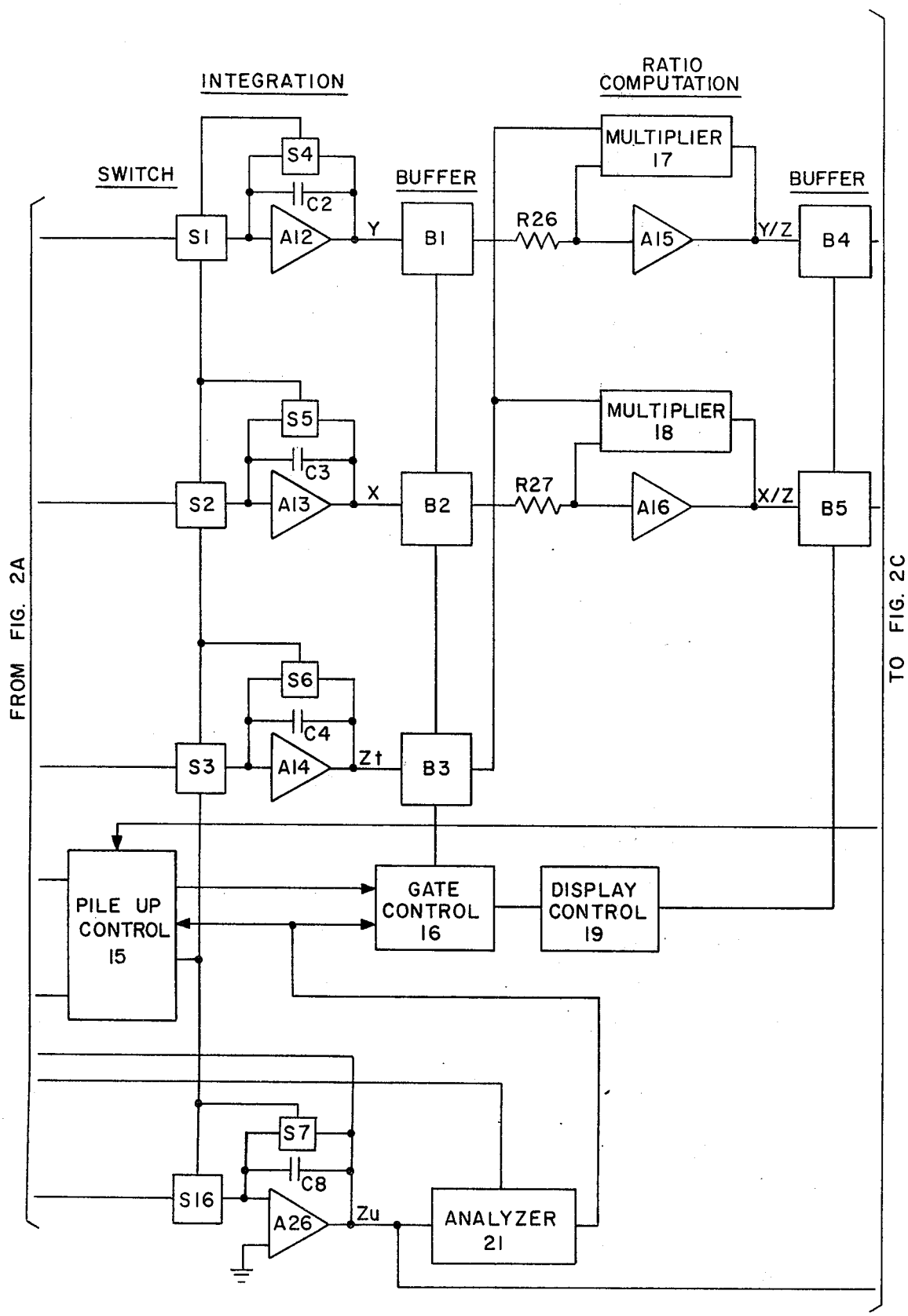
Figure 2C:
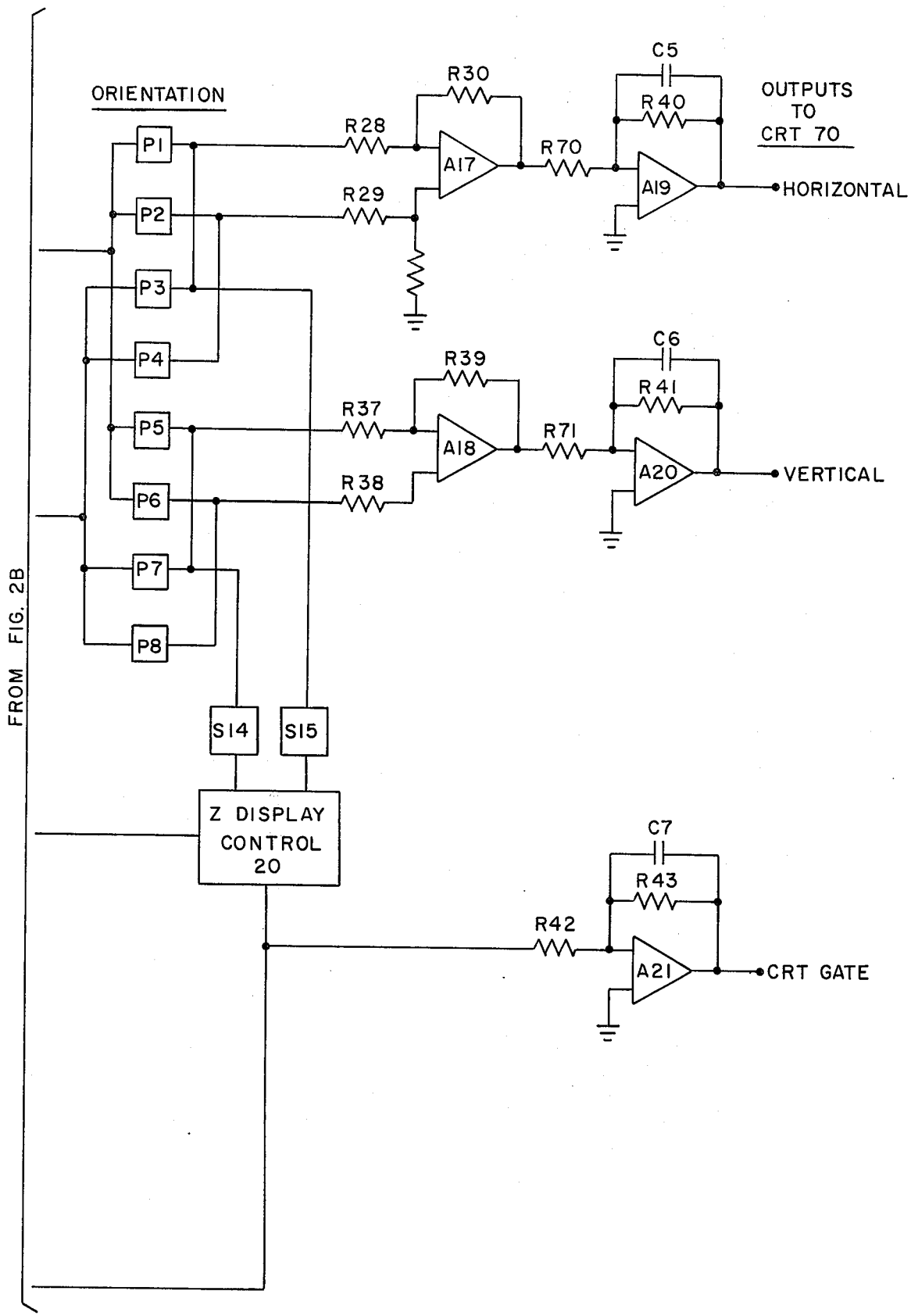

FIG. 1 illustrates a scintillation camera as heretofore described comprised of a console portion 60 and a detector portion 10. The detector portion 10 includes a detector head 50 supported in the arms of a yoke 72 mounted on an upright column 71. A collimator 75 is typically mounted on the face of the detector head 50 as illustrated. The detector head 50 is connected to the console by means of a cable harness 47. The detector console 60 includes dual cathode ray oscilloscopes 70, a control panel 11, an indicator panel 12, and position computation circuitry depicted in FIGS. 2A, 2B and 2C. With reference to FIGS. 2A, 2B, and 2C, the photodetectors, the preamp circuit, and the threshold circuit in FIG. 2A, and the orientation switches in FIG. 2C are all contained in the detector head 50 of FIG. 1. All other circuit components in FIGS. 2A, 2B, and 2C are physically located in the console 60.

Figure 3B:
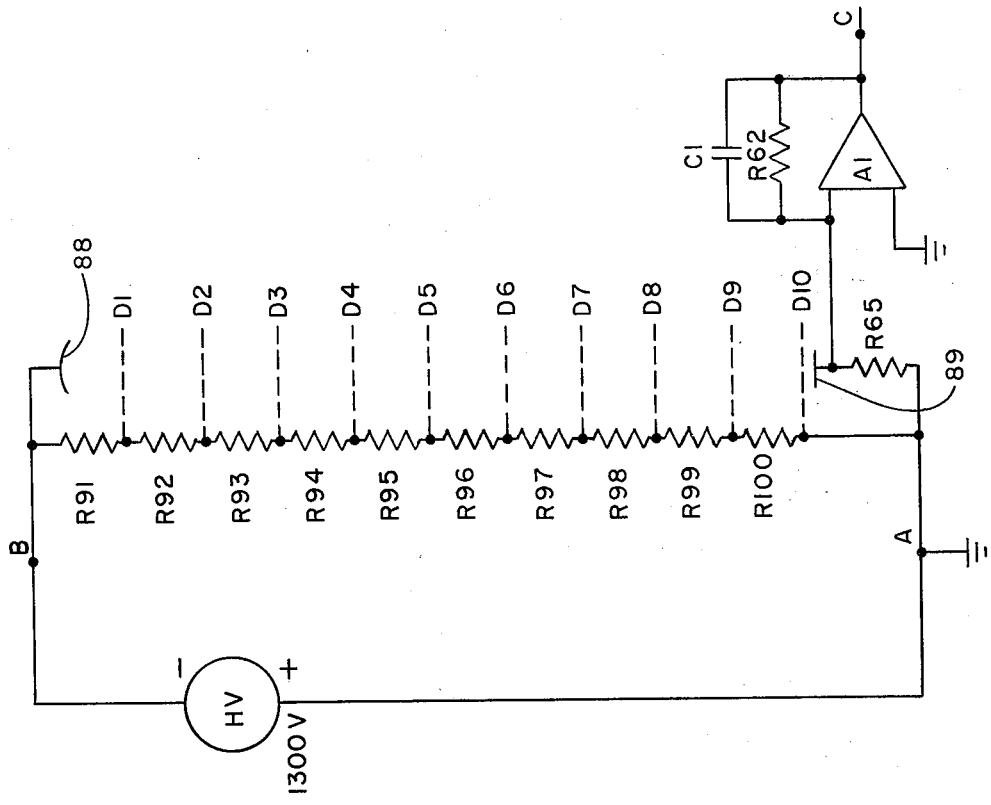

Various phototube configurations may be employed, but the most desirable arrangement is one in which phototubes, such as the phototubes PM-1, PM-2, PM-3, etc. are closely packed in a hexagonal array in the detector head 50. Typically the detector head 50 will include either 19 or 37 tubes. The phototube indicated as PM-N would therefore most typically be either PM-19 or PM-37. For purposes of simplification, only the circuitry associated with the first three phototubes is illustrated in detail in FIG. 2A, and none of the circuitry associated with the power supply for any of the phototubes is illustrated in FIG. 2A. Power supply arrangements for a single phototube are depicted in FIG. 3B.

Figure 3A:
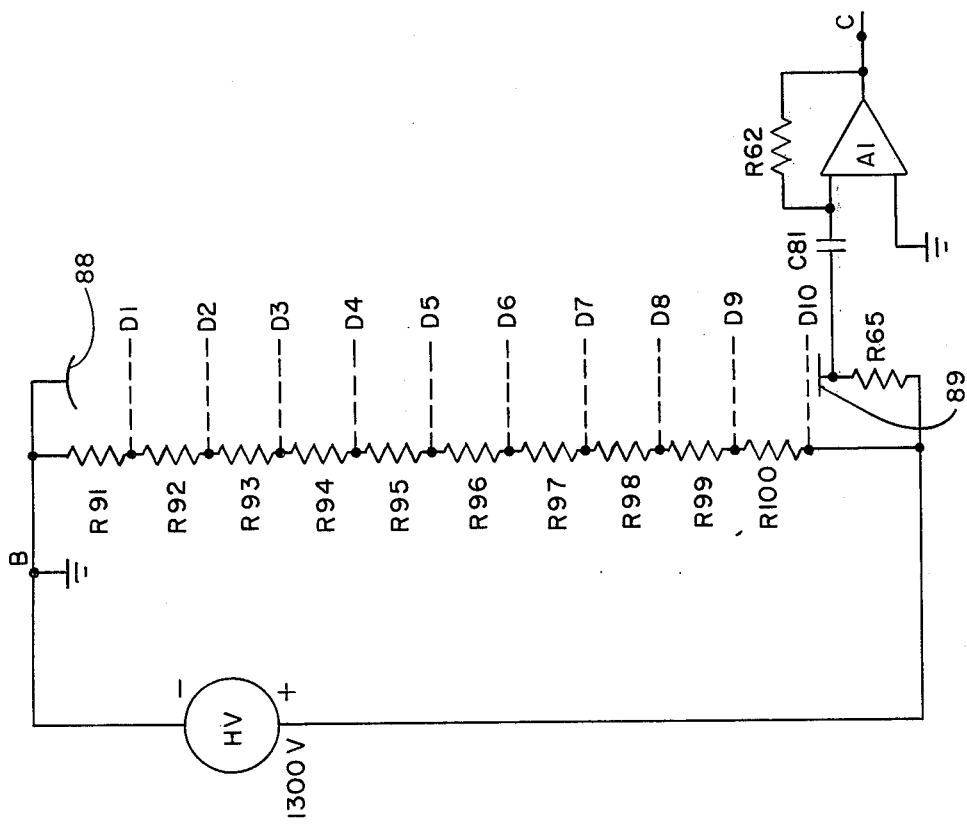
Figure 4A:
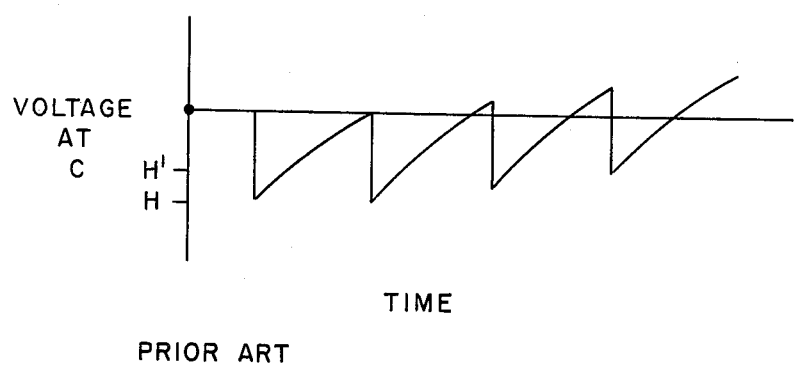
Figure 4B:
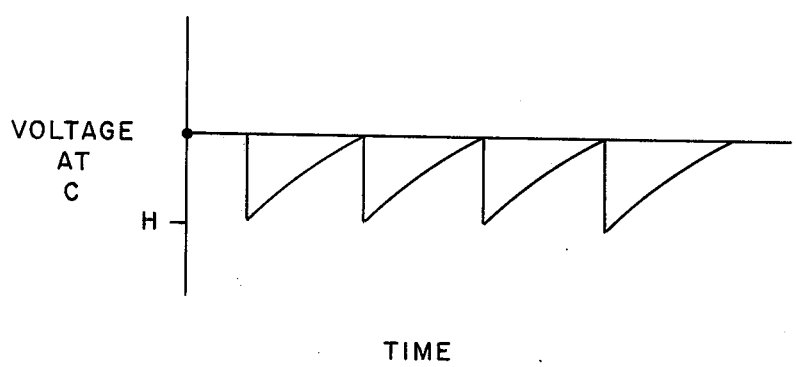

FIG. 3A illustrates a conventional arrangement in which a high voltage power supply HV of from 1300 to 1500 volts is connected to a photoanode 89 and a photocathode 88. The high voltage supply is also connected to a dynode string, including dynode stages D1 through D10 with associated resistors R91 through R100. A resistor R65 is connected between the high voltage source and the photoanode 89. In the prior art system of FIG. 3A, the photocathode 88 is connected to ground at the point B. This arrangement leads to the creation of a base line bias, however. In FIG. 4A, the amplified pulses at point C from the photoanode 89 reach an amplitude H and return to the voltage base line as indicated. However, as the rate of incident radiation increases, the pulse rate also increases. In the present invention, the anode 89 is grounded to ground at point A and the photocathode 88 is connected to a negative high voltage source as indicated. Such a connection eliminates the need for the capacitor C81 in FIG. 3A thereby eliminating the base line bias which occurs at high count rates as indicated in FIG. 4A, where there is an insufficient amount of time for the resistor R62 to bleed the positive charge off of the capacitor C81. The amplifier A1 thereby assumes an additional positive component or base line bias so that the negative pulses generated in response to detected radiation no longer produce peaks of amplitude H at point C, but instead achieve only an amplitude H'. This amplitude distortion is perpetuated and magnified at the summing stage by the integrating amplifiers A4 through A8. Moreover, background and other noise such as power supply ripple introduced into the photomultiplier system through the power supply with respect to the ground at B are amplified along with the signal pulses due to the close coupling of the power supply to the amplifier input. The same is not true with the present invention, however. In FIG. 3B, with the anode grounded at A, voltage peaks at point C are of an amplitude H as indicated in FIG. 4B, even at high count rates. In FIG. 3B, there is no base line pulse amplitude build-up into the amplifier A1. Consequently, signals of a given energy amplitude do not produce a voltage build-up as in FIG. 4A. Rather, the pulses continue to have peaks of amplitude H, as indicated in FIG. 4B. In addition, the noise in the system with respect to the ground at point A is not amplified by the dynode stages, but is passed through the system without prior amplification in the photodetector.

Returning to FIG. 2A, it can be seen that the outputs of the preamplifiers A1 are connected to a positioning matrix comprised of a plurality of resistors. In addition, the outputs of the preamplifiers A1 are connected to a threshold or non-linear amplification circuit indicated by the amplifiers A2. The output of photodetector PM-1 obtains a weighted value in a two dimensional rectilinear coordinate system by means of the resistors R11 through R14, and the resistor R15. Similarly, the output of photodetector PM-2 obtains its weighting from resistors R21 through R23, while the output of photodetector PM-3 employs matrixing resistors R31 through R35. The matrix resistors provide positional signals in a manner more fully described in U.S. Pat. No. 3,011,057 with the exception that the signals are integrated after the matrix instead of in the preamplifiers A1. The threshold amplifiers A2 each subtract a prerequisite threshold voltage from the output of the particular photomultiplier tube with which they are associated. This threshold voltage is established by means of an adjustable voltage tap at resistor R48. An amplifier A23 with a feedback loop employing a resistor R46 supplies the threshold bias to the threshold amplifiers A2.

While the outputs emanating from threshold amplifiers A2 are used for generating an actual displacement of an electron beam on a cathode ray tube, the preamplifiers A1 have direct inputs to a summing matrix which is depicted as Z no threshold or $Z_{NT}$. The output of the Z no threshold line is used for several purposes and operates upon the total energy of the pulse with no threshold value subtracted from it. This has several advantages. It provides a reference of total energy output, so that adjustments to the positional information are performed independently of the actual total pulse amplitude. Adjustments to the threshold amplifiers A2 by means of voltage tap 48 thereby have no affect on tuning of the camera, since basic tuning is performed on the basis of the $Z_{NT}$ values. This allows the percentage of the Z threshold, or $Z_T$ to be changed to improve the positioning accuracy of the matrix without detuning the camera. In this way the linearity of the camera may be easily maintained.

From the matrix resistance, voltages, in addition to being fed to the Z no threshold line and the Z threshold line, are also fed to −x, +x, −y, +y, and bias lines. The bias lines maintain a bias level to provide an operator bias to the threshold output of the preamplifier means of a voltage source acting through resistors R19 and R20 and through an amplifier A3, A4, A5, A6, A7 and A8 having a feedback loop through resistors R18, R16, R17, R24, R25 and R36 respectively.

The information from the matrix resistors is passed to a plurality of stages of buffer storage for electrical pulses produced in response to detected radiation. In this manner, the position computation circuitry is operative to accommodate statistical fluctuations in the rate at which pulses are received for processing. To reach the buffer storage stages, the electrical pulses from the matrix resistors are passed to a series of summing amplifiers A4 through A8, having respectively associated therewith feedback resistors R16, R17, R24, R26 and R36. These summing amplifiers consolidate the positional information. Amplifier A4 sums the +y pulses, while amplifier A5 sums the −y pulses. Amplifier A6 sums the +y pulses, while the amplifier A7 sums the −x pulses. Amplifier A8 sums the Z threshold values. The +y and −y outputs are further summed in an amplifier A9 while the +x and −x outputs are summed in amplifier A10. The bias level and $Z_T$ are summed in amplifier A11.

The bias set up by the circuit employing the amplifier A3 is designed to take excess current. The threshold circuit, including the amplifiers A23 and A2, is actually a current source. Regardless of the position of a quanta of radiation, an identical amount of current is generated in the resistor matrix upon the receipt of each electrical pulse exceeding the threshold value, and the amount of current that is not needed by the $Z_T$, −x, +x, +y, and +y circuits is shunted off through the bias resistor R20. Resistor R20 is chosen to allow a total impedance of 500 ohms at the output of the threshold amplifier circuit. That is, the sum of all the resistors in the output of each thresholded preamplifier portion totals 500 ohms in parallel. This causes the output of the preamplifier section to appear to be a voltage source instead of a current source. This allows the matrix resistors R11, R12, etc., to determine the portion of the current flowing through each of them.

After passing through the summing stage, the +y and −y outputs are combined and the +x and −x outputs are combined by means of amplifiers A9 and A10 respectively, as previously noted. The amplifier circuit A9 takes the +y and −y inputs and generates a bi-polar signal for y. Likewise, the amplifier A10 generates a signal from the +x and −x input. A Z output is produced by the amplifier A11. The amplifiers A9, A10 and A11, due to their common mode rejection, also remove their bias at their input due to resistors R19 and R20. The outputs of amplifiers A9, A10, and A11 are passed to the first stage of buffer storage. This first stage of buffer storage takes the form of an integration circuit for receiving and integrating pulses emanating from the photodetectors. The integration circuit for the y pulses includes an amplifier A12, and a capacitor C2 connected in parallel. Similarly, the integration circuit for the x pulses includes an amplifier A13 and capacitor C3 while the integration circuits for the Z pulses includes an amplifier A14 and a capacitor C4. Integrator reset means in the form of switches S4, S5 and S6 are provided for resetting the integration circuits at a determinable interval of time subsequent to detection of the associated quanta of radiation by the scintillation crystal. Also, the input switches S1, S2 and S3 respectively serve as means for disconnecting these integration circuits from the photodetectors while holding signals in these integration circuits of this first buffer storage stage.

A second buffer stage is comprised of sample and hold circuits B1, B2 and B3, which are connected to the outputs of the integration circuits. Sample and hold circuits B1, B2 and B3 include timed gating devices and receive integrated signals from the amplifiers A12, A13 and A14 respectively, prior to actuation of the integrator reset switches S4, S5, and S6. The circuits B1, B2 and B3 hold the signals received from the integrators for a preset minimum time long enough for the computation circuits to settle to final value. The computation circuits for computing the ratio of $Y \div Z_T$ and $X \div Z_T$ are preceded respectively by resistors R26 and R27, receive inputs from the buffers B1, B2 and B3 and generate responsive position registration signals. The computation circuit for determining the ratio $Y \div Z_T$ includes a multiplier circuit 17 coupled in the feedback path of amplifier A15. The computation circuit for determining the ratio $X \div Z_T$ includes a multiplier circuit 18 coupled in the feedback path of amplifier A16. The outputs of these computation circuits are respectively passed to a third buffer stage, formed of signal storage circuits B4 and B5. The buffers B4 and B5 receive the position registration signals from the computation circuits and activate the registration means, formed of a device for graphically depicting the relative location of quanta of radiation detected by the scintillation crystal. The position registration signals are thereby depicted on the registration means as the locations at which quanta of radiation are detected. As previously noted, the registration means typically takes the form of a cathode ray tube or oscilloscope 70 the face of which represents the scintillation crystal of the detector head 10.

Figure 6:
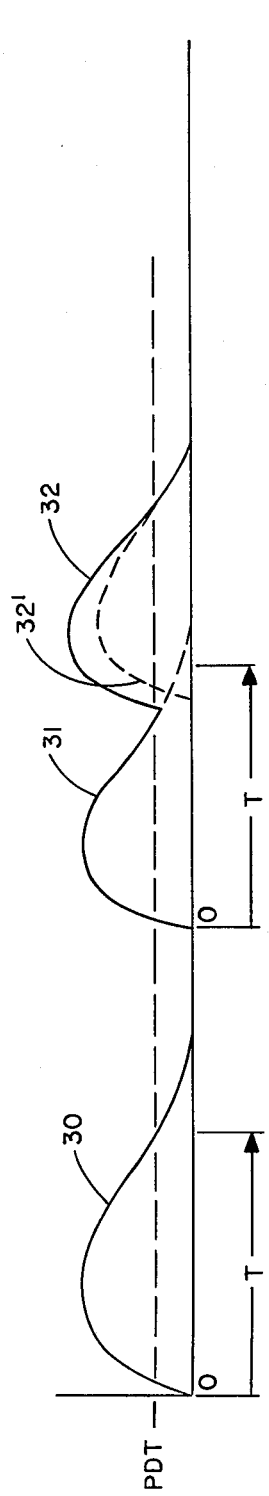
Figure 6A:
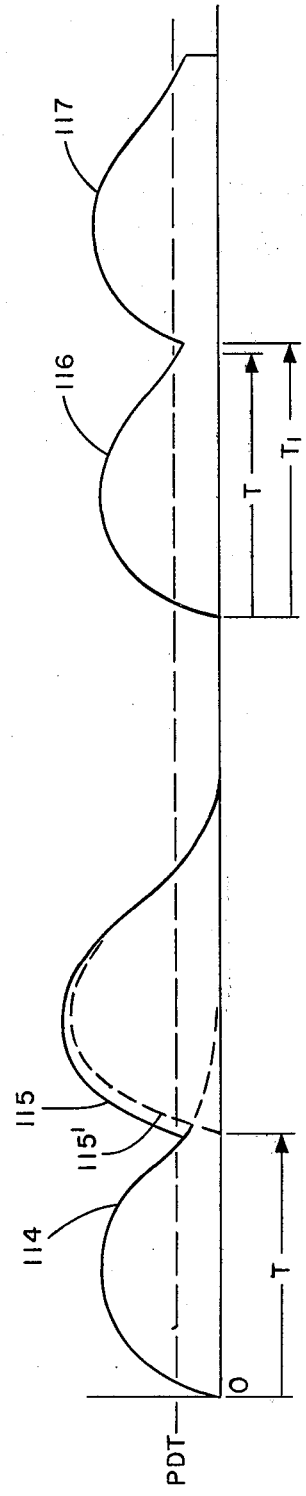

The input switches S1, S2 and S3 to the first buffer stage integration circuits allow the integration circuits to be disconnected from the photodetectors in the detector head 50 from the time that a single scintillation in the crystal is detected until processing of the resulting pulses is completed. If another scintillation occurs while the integrator information from the prior scintillation is being analyzed, the second event will not change the values in the integration circuits. This would otherwise occur despite the operation of pulse pile-up control circuit 15 when pulses are separated by an interval of time such that they are not piled-up sufficiently to actuate the pile-up control circuit 15, but are sufficiently close in time so that the charges in the integration circuits would be changed. An example of the alternation that would occur in conventional RC integration circuits is illustrated in FIG. 6A. A charge 114 in one of the integrators of the first buffer stage begins at a time designated as zero. After interval T the charge has dropped below the level PDT so that a second pulse is not rejected by the pulse pile-up control circuit 15. However, immediately thereafter the second pulse begins to cause the build up of a charge 115 in the conventional integration circuit. This charge build up occurs in the form depicted at 115, which is altered from the form 115', which it would otherwise assume were it not for the lingering tail of the first pulse 114. In the present invention, however, the integration circuit is disconnected from the photodetectors so that the charge 117 from the second pulse cannot begin building up until one of the switches S1, S2 or S3 reconnects the integration circuit to the photodetectors. This occurs at time $T_1$, which is the time instant at which the previous charge in the integration circuit is dumped, so that there is no effect on the second charge 117 by virtue of the prior charge 116. With the RC type integrator circuits used in conventional scintillation cameras the integration circuits are not disconnected from the photodetectors and the values of the integration circuit charges are susceptible to alteration by subsequent pulses. The dump switches S4, S5 and S6 provide the integration circuits of the present invention with a further advantage in operation over the conventional RC integration circuits by getting the integrator ready to receive a new pulse very quickly. With the RC integrator, the discharge time must be slow so that pulses do not change much during the analyzing time. This results in increased dead time in system operation.

In conventional cameras when the integrating is done in the preamplifiers in the detecting head 50, the use of dump switches would require the provision of one dump switch per preamp, which would not be too practical. By matrixing the current signals and integrating after the matrix, the number of integration circuits is reduced which allows a fewer number of dump switches S4, S5 and S6 to be used. The signal out of the matrix and integration circuits in both cases is the same, since the signal sum produced in a system with integrating preamplifiers ($\Sigma[\int fx_1 + \int fx_2]$) is equal to the signal sum produced with the present invention ($\int \Sigma[fx_1 + fx_2]$).

As signals are generated by the amplifiers A9, A10 and A11, they are gated to the associated integration circuits by means of switches S1, S2 and S3 respectively. Current is thereby allowed into the amplifiers A12, A13 and A14. These amplifiers generate a wave form and hold it flat so that it can be analyzed if required. In addition, the switches S1, S2, and S3 also actuate the timing mechanisms of the reset switches S4, S5, and S6. After a determinable interval of time subsequent to detection of the associated quanta of radiation by the scintillation crystal, the switches S4, S5 and S6 discharge the wave form respectively held in capacitors C2, C3 and C4, bringing the signal in the associated integration circuit back to O. It should be noted that an equivalent integrate and dump circuit is operative in conjunction with the analyzer 21. That is, a gating switch S16 opens an integrating amplifier A26 employing a current integrating capacitor C8. After a timed interval, the reset switch S7, which was actuated by the switch S16, discharges the contents of capacitor C8 back to zero. This integration amplifier circuitry is operative upon the value of the Z pulse measured without threshold ($Z_{NT}$). The switch S16 also controls the operations of the switches S1, S2 and S3.

A decision as to whether or not signals will be passed from the integration circuits to the buffers B1, B2 and B3 is made by the analyzer 21. Analyzer 21 looks at the integrated value $Z_U$ of the unthreshold Z signal, from the integrating amplifier 26 to see if it falls within the energy window which the user has determined to be acceptable. If $Z_U$ is acceptable, the analyzer 21 actuates the gate control circuit 16 which in turn opens gates to the sample and hold circuits B1, B2 and B3. The integrated signals from the integrating amplifiers A12, A13 and A14 are then allowed to enter the sample and hold circuits B1, B2 and B3 respectively. If no actuating signal is received from the analyzer 21, the gates to circuits B1, B2 and B3 are not opened, and switches S4, S5 and S6 erase the information contained in the integration circuits for the y, x, and $Z_T$ pulses. When an actuating signal is received from analyzer 21, and buffers B1, B2 and B3 are loaded respectively with the y, x, and $Z_T$ signals, the switches S4, S5 and S6 apply the discharge signals to the integration circuits, and the integrators are discharged and are thereafter free to handle subsequent input pulses.

The sample and hold circuits B1, B2 and B3 hold their respective signals for the amount of time that is required by the computation circuitry to perform the necessary corrections to the input positional information. In the computation circuits, the $Z_T$ signal, which is proportional to the pulse energy, is fed as an input into the multiplier circuits 17 and 18, which are respectively connected in the feedback paths of amplifiers A15 and A16 to effectively form dual dividing networks. The y signal from sample and hold circuit B1 and the x signal from sample and hold circuit B2 are passed respectively to circuits 17 and 18 as inputs. The outputs of circuits 17 and 18 are then the quotients respectively of the y signals divided by $Z_T$ and the x signal divided by $Z_T$, independent of energy. The circuits 17 and 18 operate over a full wide dynamic range of input energies from 50 KeV up to 680 KeV. The corrected y and x signals are respectively passed from the computation circuitry to the signal storage buffers B4 and B5, thereby freeing the computation circuits for further processing. The corrected y and x signals are held in the buffers B4 and B5 for further processing, which occurs through the orientation circuits P1 through P8. The orientation circuits P1 through P8 take the corrected x and y output and feed them to the horizontal and vertical deflection controls of the cathode ray beam after coordinating them with the orientation of the patient with respect to the scintillation crystal of the detector head 10. The circuits P1 through P8 include push button switches which are physically located around the periphery of the scintillation crystal on the detector 10, so that there can be no confusion in coordinating the orientation of the patient with the CRT display 70. Display requires approximately 2 microseconds of time, during which the computation circuits are reading another pulse for display.

The buffer storage devices depicted thereby form three stages of buffer storage. The integration circuits employing the amplifiers A12, A13, and A14 function as one buffer storage stage. The sample and hold circuits B1, B2 and B3 function as the second buffer storage stage, while the buffers B4 and B5 form the third buffer storage stage. In this way, the system can accommodate pulses emanating from several quanta of radiation detected in rapid sequence. Such rapid sequential detection occurs not only when measuring radiation from a source of high activity, but also by virtue of statistical variations in the occurrence of radioactive events in sources of lower activity. That is, while there may be a fairly lengthy interval on the average between radioactive emissions from a radiation source, the length of time between sequential emissions will vary, and such statistical variations will, upon occasion, produce radioactive emissions in rapid sequence. The plurality of buffer stages provided by the present invention forms a derandomizing buffer in which the input signals arriving at random can be fed to a display system which has a different "dead time", or processing time, than the position computation circuitry.

Figure 5:
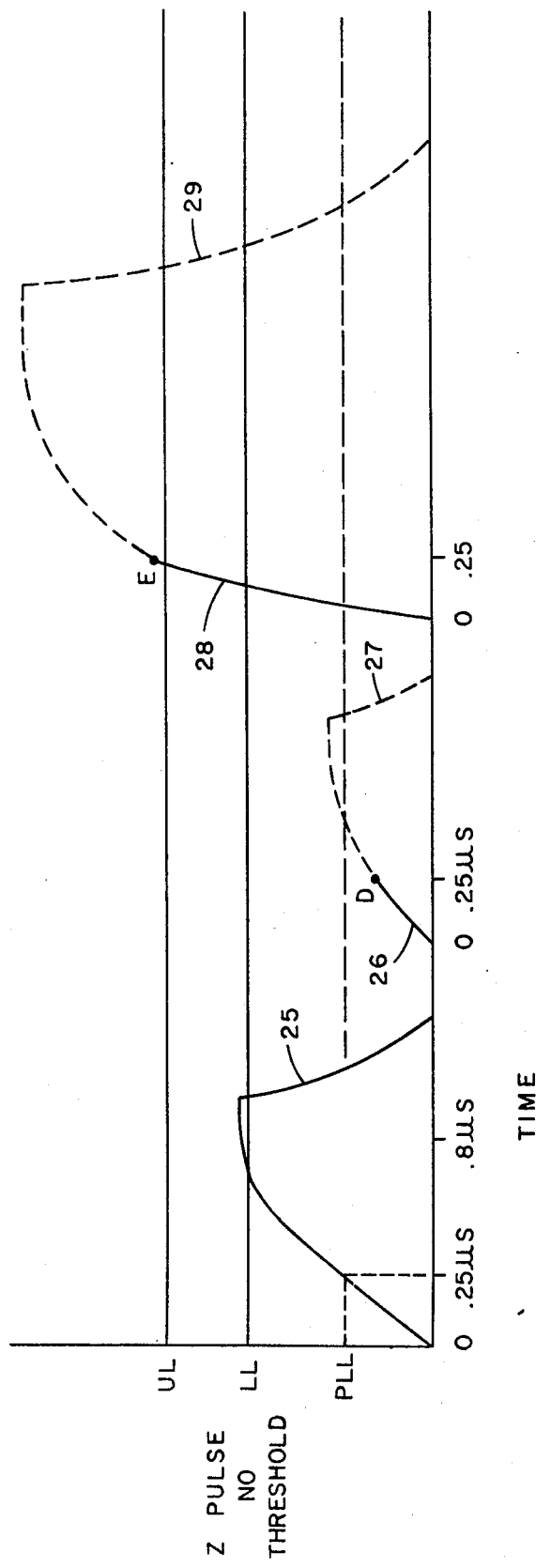

The part of the position computation circuitry in the lower portion of FIG. 2B depicts the analyzer 21 and circuitry associated therewith. The analyzer 21 includes a differential discrimination means for defining the specific energy range of interest to the user of the scintillation camera. This device for differential discrimination operates on the pulse amplitude peaks of pulses generated in response to quanta of radiation detected by the scintillation crystal in the detector head 10. The analyzer 21 also includes a preliminary differential discriminator means for rejecting pulses and provisionally accepting pulses on the basis of pulse amplitude measured prior to pulse peaking. The analyzer 21 is illustrated in detail in FIG. 7 and the operation of the preliminary differential discriminator is illustrated in FIG. 5. The circuitry for the differential discriminator means defining a specific energy range of interest includes a midrange energy selector and associated circuitry for selecting a median energy setting. The circuitry for the midrange energy selector is formed of an adjustable voltage tap resistor R58 in FIG. 7 connected to an amplifier A23. The output of amplifier A23 is connected both to an input of a comparative output amplifier means and to a window width selector circuit. The window width selector circuit includes an adjustable voltage tap from resistor R61 connected to a proportional amplifier circuit. The proportional amplifier circuit includes a multiplier circuit 23 with inputs from the median energy marker amplifier A23 and from the voltage tap at resistor R61. The ouput of the multiplier circuit 23 is thereby equal to a predetermined percentage of the output of the midrange energy selector circuit. This percentage is determined by the user in setting the window width selector circuit, while the midpoint or median energy setting of the energy range of interest is selected by the user by adjustment of the midrange energy selection circuit.

The output of the multiplier circuit 23 is passed to an amplifier A25 having a feedback loop with a resistor R51. The output of amplifier A25 is then divided into dual outputs, one of which is connected to a unity gain inverting amplifier A36. Resistors R56 and R57 ensure outputs of equal amplitude but opposite polarity to the amplifiers A27 and A29. The amplifier A27 establishes the upper discriminator level while the amplifier A29 establishes the lower discriminator level for the energy range of interest. In this way a mid-point of the energy range of interest is selected while the upper and lower discriminator levels are established at equal percentages from the median energy setting measured with respect to ground by means of the window width selection circuit.

The window width selection circuit thereby acts as an adjustable window width selector which adjusts the upper and lower discriminators to levels which are respectively above and below the median energy established by the mid-range energy selection circuit by equal percentages of the median energy measured with respect to a base reference.

The $Z_{NT}$ pulses are extracted from the resistor matrix as indicated in FIG. 2A, and are passed through amplifiers A24 and A25 to a switch S6. A feedback resistor R52 is associated with amplifier A24. The amplified $Z_{NT}$ pulses are passed to an integrating amplifier A26 employing an integrating capacitor C8 as previously described. The output of this integration circuit is denoted as $Z_U$ and is passed both to the Z display control circuit 20 and a CRT gate in FIG. 2C and to the analyzer 21. To actuate the CRT gate, the output of amplifier A26 is passed through a resistor R42 and another integration circuit comprised of an amplifier A21, a resistor R43, and a capacitor C7. Unless pulse rejection is caused by the analyzer 21, the integrated output from amplifier A21 will actuate generation of the CRT beam when positional signals have been received from the buffers B4 and B5. The output of amplifier A26 which is passed to the Z display control circuit 20 causes display control signals to be generated and passed to the inputs of feedback amplifiers A17 and A18 as shown. Resistors R28 and R29 lie between the inputs of amplifier A17 and the orientation switches while comparable resistors R37 and R38 are located at the inputs of amplifier A18. Feedback resistors R30 and R39 complete feedback loops to amplifiers A17 and A18 respectively. An integration circuit connected to the output of amplifier A17 completes the horizontal deflection circuit. This integration circuit is formed of an amplifier A19, resistors R40 and R70, and a capacitor C5. The X deflection is thereby imparted to the CRT beam by virtue of the contents of buffer B5 upon receipt of a display control signal from circuit 20, subject to orientation correction by the orientation switches P1 through P4. An analogous integration circuit is formed of an amplifier A20, resistors R71 and R41, and capacitor C6. This intgration circuit imparts Y deflection to the CRT in response to the contents of buffer B4. Orientation switches P5 through P8 ensure that the correct orientation exists with regard to the Y deflection signal. Timing switches S14 and S15 remove the actuating output from the Z display control unit 20, after a predetermined interval of time.

As previously stated, the $Z_U$ output from amplifier A26 is passed to the amplifier A21. The $Z_U$ pulses are passed through a resistor R53 to the comparative output amplifier A22 having an opposing input connected to ground through resistor 55. The input $Z_U$ is no longer a pulse, but a steady stage negative voltage level. Connected to the same input of the amplifier A22 is the positive voltage level from the median energy marker amplifier A23 established by the mid-range energy selection circuit. This voltage level acts through resistor R59 and serves as a base level. If the level of $Z_U$ is equal to the base level, there is zero output from the comparative output amplifier A22. If the level of $Z_U$ is above or below the base level, a positive or negative output emanates from the amplifier A22. A resistor R54 is associated with amplifier A22 in a feedback loop. The output of amplifier A22, if any, is passed as an input to amplifiers A27, A28, A29 and A30. If the pulse creating the voltage $Z_U$ was of an energy lying between the mid-point of the energy range of interest and the upper discriminator level thereof, the amplifier A27 produces an output which is passed to an inverting AND gate 1 and to an inverting amplifier A31. Amplifier A29 also produces an output which, together with the output from inverting amplifier A31, gates an AND gate 2 which triggers operation of the automatic gain adjustment circuit 22. If the level of the output of amplifier A22 lies between the upper level discriminator or below the lower level discriminator, neither the amplifier A27 nor the amplifier A29 will produce outputs. This means that no gating pulse will be passed to the display control circuit 19 to allow unblanking of the CRT display. AND gates 4 and 5 respectively indicate that the level of $Z_U$ is between the energy mid-point setting and the upper or lower discriminator level. AND gates 4 and 5 are actuated by AND gate 2 in combination with an output from either inverting AND gate 32 or directly from amplifier A28. If the processed pulse is within the energy window, and is not exactly equal to the mid-point of the energy range of interest, the amplifier A28 will produce an output which will trigger an automatic feedback adjustment through the automatic gain adjustment circuitry 22 to maintain the median energy marker at the mid-range setting, and to maintain the median energy marker and the upper and lower discriminators in the prescribed relationship. This is accomplished by means of up-down counters within the automatic gain adjustment circuit 22 which, after a prescribed number of counts one way or the other, will produce an adjustment output which acts on the amplifiers A23, A22 and A24. In this manner, an energy peak of a detected radiation source can be maintained at the level established by the mid-range energy selection circuit, and the distribution of pulses about that peak can be centered in the energy window.

Figure 7:
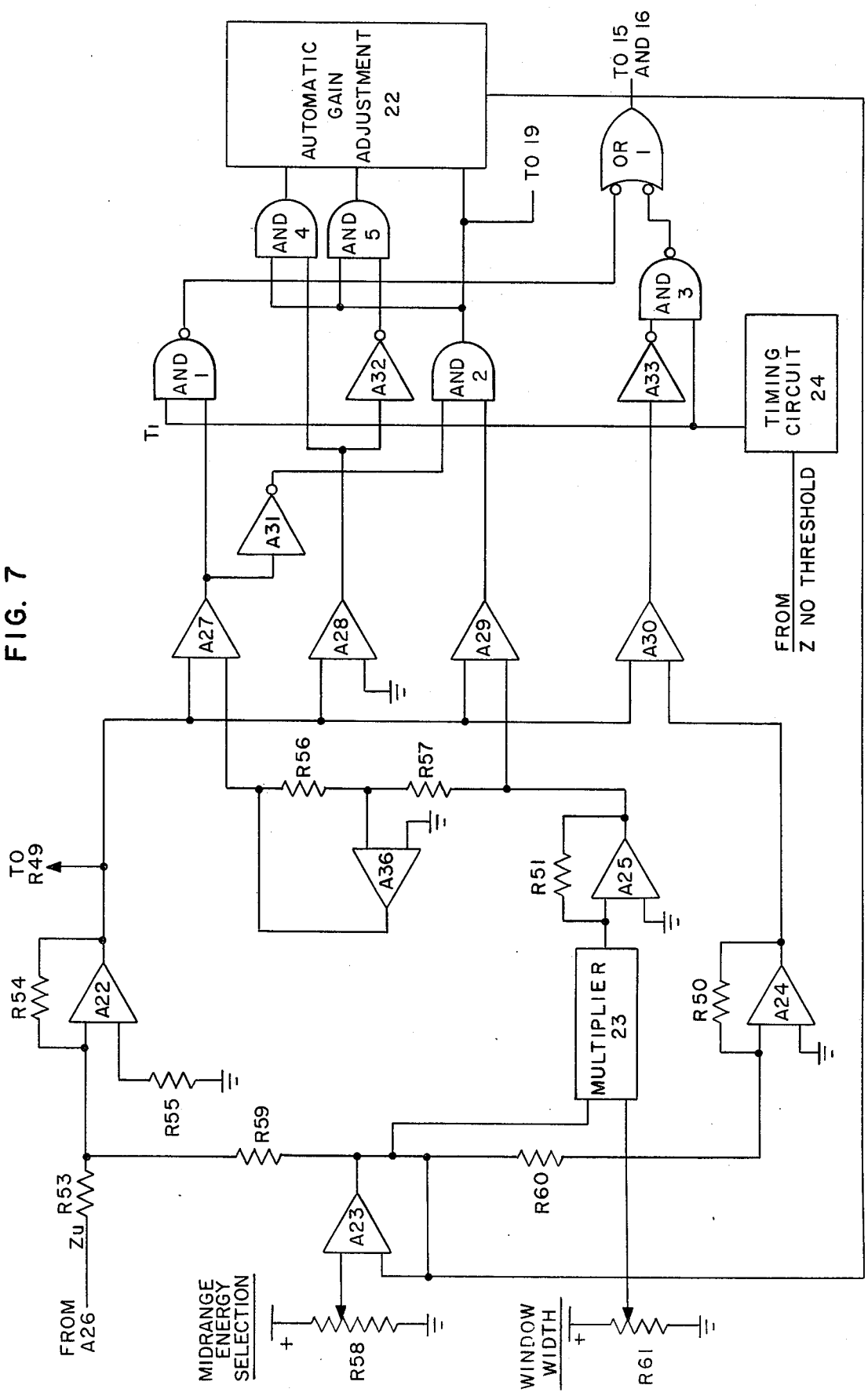

In addition to the energy peaking characteristic of the system, the circuit depicted in FIG. 7 provides for the early determination of the acceptability of pulses detected by the photodetectors. Specifically, there is provided a preliminary differential discriminator means including the amplifier A30 which is connected to receive pulses from the photodetectors and to provide a gating signal to the sample and hold circuits B1, B2 and B3. The gating signal is generated only under specific conditions. That is, the signal is generated only when the sum of the pulses from the photodetectors, measured at a predetermined time after detection of the associated quanta of radiation and before the sum reaches its amplitude peak, lies within an acceptable energy range selected for purposes of preliminary amplitude determination. In the circuitry of FIG. 7, the amplifier A30 receives an input from the amplifier A24 through resistors R59 and R60. The output of amplifier A30 is determined by a comparison of this input with the output from the amplifier A22. The amplifier A30 makes a preliminary determination as to whether the signal looks as though it will fall within the energy window between the levels UL and LL in FIG. 5. The integration circuit formed by the amplifier A26 and capacitor C8 in FIG. 2B is open for a specific amount of time, usually about 0.8 microseconds during which time the integrator charge is built up to about 99% of the total available signal from the photodetectors. During a portion of this time, for example about the first quarter micro-second, the integrator has built up to approximately 50% of the total signal out of the photodetectors. At this quarter microsecond point in time, the integrator is compared with a value equal to a predetermined fraction of the level LL. The level LL is the minimum pulse load that will ultimately be acceptable to the system as being within the energy range of interest. If the signal at amplifier A30 is slightly below this predetermined value, which may be, for example, about 50% of the lower discriminator setting, it is apparent that there is no chance that the integrated output will rise to the lower level of the energy range of interest at the termination of the full integration period. It is therefore appropriate to immediately discard this pulse and reset the integrators so that the system is ready to receive and process a new pulse. This is accomplished by the amplifier A30, the inverting amplifier A33, the inverting AND gate 3 and the timing circuit 24 which provide an output to OR gate 1 only when the amplitude of the integrated pulse value fails to rise to about 50% of the lower discriminator setting LL.

Also, if during the integrating time the integrator should exceed the upper level UL of the window, there is no point in integrating the whole period of time since the pulse will in any event lie above the energy range of interest. In this case, a signal from the inverted AND gate 1 reaches OR gate 1 as an input, thus causing the pulse to be dumped immediately and the position computation circuitry to be reset. For those pulses which do not exceed the upper level UL, but which do achieve at least a predetermined percentage PLL (such as 50%) of the lower level LL after a predetermined time (for example about 30% of the time interval of signal integration), then integration is carried out for the full period of time. This allows the integrators to settle for a short period of time and compare them against discriminators to determine whether or not they are in the window as previously described.

The operation of this preliminary differential discriminator means is illustrated by way of example in FIG. 5. An integrated value of a pulse at the integration circuit formed by amplifier A26 and capacitor C8 is indicated at 25 in FIG. 5. The preliminary differential discriminator effects amplitude measurement after about 0.25 microseconds, which is about 30% of a .8 microseconds, which is the time interval elapsed between the time of detection of a quanta of radiation and the time at which integration of the total available pulse signal as to the integration circuit reaches about 99% of its total amplitude. This amplitude measurement shows that the level of the pulse 25 has achieved the level PLL, which is about 50% of the lower discriminator setting LL of the differential discriminator defining the specific energy range of interest. From this determination, it is known that the pulse 25 has a sizeable likelihood of falling within the energy range of interest. Therefore, integration is carried out for the full integrating interval. On the other hand, when a small pulse, such as the pulse 27 is received, measurement after about 0.25 microseconds shows that this pulse has achieved only amplitude D, which is less than the requisite preliminary amplitude level PLL. Processing of this pulse is immediately terminated, the pulse is dumped, and the circuitry is ready for processing subsequent pulses. Similarly, measurement of the pulse 28 after about 0.25 microseconds shows that while this pulse has indeed exceeded the level PLL it has also exceeded the upper discriminator level UL. This pulse, therefore, cannot lie within the energy range of interest. Therefore the pulse 28 is also immediately dumped and the circuitry readied for processing subsequent pulses.

Figure 5A:
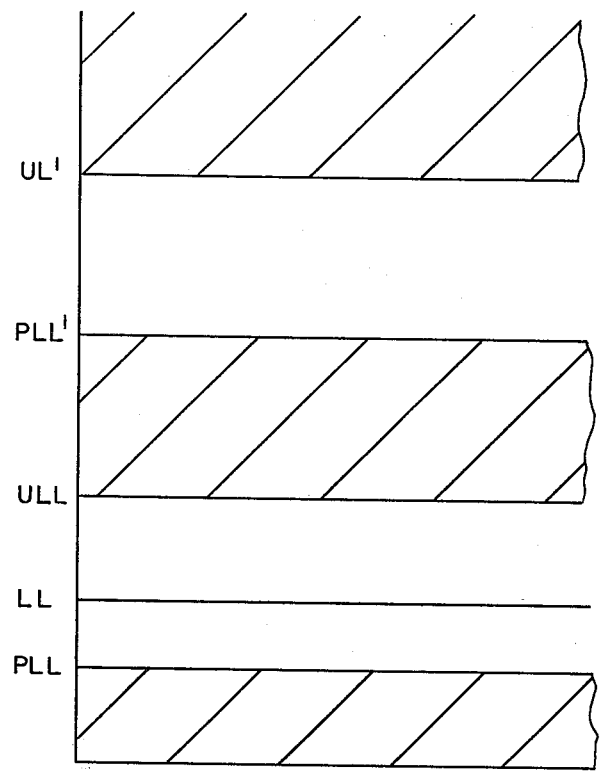

While pulses will be fully processed if preliminary measurements shows an amplitude falling within the range defined by the energy levels UL and PLL in FIG. 5, it is sometimes advantageous to define discontinuous energy bands for preliminary amplitude measurement. A specific instance would be in the case of dual isotope measurement. In this instance, it would be advantageous to employ a plurality of preliminary differential discriminator devices having different upper and lower discriminator levels to delineate energy bands within which pulses are rejected. For example, in FIG. 5A pulses are rejected if they lie below the energy level PLL, if they lie between the energy levels PLL' and ULL, and if they lie above the energy level UL'. Pulses are accepted for full processing at the time of preliminary measurement only if their amplitudes lay between the bands defined by PLL and ULL or between PLL' and UL'.

The position computation circuitry of FIGS. 2A, 2B and 2C also includes means for detecting the concurrent existence of electrical pulses emanating from the detection of different quanta of radiation, and means for preventing the registration of locations of those different quanta of radiation. Such a situation is comonly termed "pulse pileup" and is graphically depicted in FIG. 6. The curve 30 depicts a pulse detected by the photodetectors and integrated by the integration circuits as previously described. The curve 30 represents the pulse as it is held for processing and then as it decays through actuation of one of the switches S4, S5, S6, or S7. However, instances occur where pulses, such as the pulse 31, do not conclude decay before subsequent pulses, such as the pulse 32, are received. In such a situation, the pulse 32 rides on top of the tail of the decaying pulse 31 and appears larger in amplitude and more distorted in decay than it would were it to have occurred in isolation, as indicated at 32'. The result of an occurrence such as the pile-up of pulse 32 on pulse 31 is likely to be the display of an erroneous signal on the oscilloscope 70 of the scintillation camera. To avoid this, a comparator circuit means is provided for comparing the output amplitude of the integration circuit with an acceptable amplitude level related to the predictable pulse decay rate. This comparator circuit device is illustrated in FIGS. 2A and 2B as a pulse pile-up control circuit 15 with inputs from differential amplifiers A34 and A35. The $Z_{NT}$ pulse is used as a trigger for each of these amplifiers. The output of the integration circuit formed by amplifier A26 and capacitor C8 is fed to amplifier A35 along with the $Z_{NT}$ pulse, but has a voltage tap connected to resistor R44 for establishing an acceptable amplitude level designated PDT in FIG. 6. The amplitude level PDT is related to the predicted pulse decay rate. An output from the timing circuit 24 of the analyzer 21 determined the time T at which the amplitude of the amplifier A35 is compared with the acceptable amplitude PDT. If the pulse has decayed and there is no pulse pileup, the input from amplifier A35 will be less than that from A34, and processing of the pulse will be allowed to continue If, however, a situation has occurred in which a pulse 32 is riding on a prior pulse 31, the output of the amplifier A35 will exceed the output of the amplifier A34, since the pulse amplitude will exceed the level PDT. In this instance, the pile-up control circuit 15, which acts as a pulse rejection device, discards the pulses present in the position computation circuitry. This is done by the generation of reset signals to the gate control circuit 16 and to the switches S1, S2 and S3, which in turn respectivey actuate reset switches S4, S5 and S6. The gate control circuit resets the sample and hold buffers B1, B2 and B3.

The foregoing embodiment has been depicted for purposes of illustration only, and it is to be understood that various modifications thereto for increasing the maximum pulse acceptance rate may be made and still be encompassed within the scope of the invention as claimed.

I claim as my invention:

1. In a scintillation camera employing an array of photodetectors viewing overlapping portions of a scintillation crystal and producing electrical pulses in response to quanta of radiation impinging upon said scintillation crystal, and position computation circuitry for processing said pulses to register the relative locations of quanta of radiation detected by said crystal within a specific energy range of interest, wherein said position computation circuitry includes electrical components defining an intrinsic maximum rate of acceptance of said pulses for processing, the improvement comprising means including a plurality of stages of buffer storage each stage adapted to process separately electrical pulses produced in response to each detected radioactive event of interest, whereby said position computation circuitry is operative to increase the intrinsic maximum rate of acceptance of pulses for processing by accommodating statistical fluctuations in the rate at which pulses are received for processing.

2. The scintillation camera of claim 1 wherein there are provided integration circuit means for receiving and integrating pulses emanating from said photodetectors, means for disconnecting each of said integration circuits from the photodetectors while holding integrating signals therein, integrator reset means for resetting said integration circuit means after a determinable interval of time subsequent to detection of the associated quanta of radiation by said scintillation crystal, sample and hold circuit means with timed gating means connected to said integration circuit means for receiving an integrated signal therefrom prior to the actuation of said integrator reset means and holding the signal for a preset time interval sufficient to allow said electrical components to settle, computation means receiving inputs from said sample and hold circuit means and generating position registration signals in response thereto within the aforesaid timed interval associated with said sample and hold circuit, registration means for graphically depicting the relative locations of quanta of radiation detected by said crystal, and signal storage means for receiving said position registration signals from said computation means and for actuating said registration means to depict the aforesaid locations.

3. The scintillation camera of claim 1 wherein said position computation circuitry includes differential discriminator means for defining the aforesaid specific energy range of interest based on the pulse amplitude peaks of pulses generated in response to quanta of radiation detected by said crystal, and preliminary differential discriminator means for rejecting pulses and provisionally accepting pulses on the basis of pulse amplitude measured prior to pulse peaking.

4. The scintillation camera of claim 3 wherein said position computation circuitry includes integration circuit means for receiving and integrating pulses emanating from said photodetectors, integrator reset means for resetting said integration circuit means at a determinable interval of time subsequent to detection of the associated quanta of radiation by said scintillation crystal, sample and hold circuit means having an input gate and having timed gating means and connected to said integration circuit means for receiving an integrated signal therefrom, when gated, and for holding said integrated signals for a timed interval after receipt thereof prior to actuation of said integrator reset means, and wherein said preliminary differential discriminator means is connected to receive pulses from said photodetectors and to provide a gating signal to said sample and hold circuit means only when the sum of the aforesaid pulses from said photodetectors, measured at a predetermined time after detection of the associated quanta of radiation and before the aforesaid sum reaches its amplitude peak, lies within an acceptable amplitude range selected for purposes of preliminary amplitude determination.

5. The scintillation camera of claim 4 wherein said preliminary differential discriminator means is adjusted to effect amplitude measurement when about 30% of the time interval has elapsed between the time of detection of a quanta of radiation and the timed interval associated with said sample and hold circuit means.

6. The scintillation camera of claim 5 wherein said preliminary differential discriminator means is adjusted to generate a gating signal to said sample and hold circuit only when the amplitude of the aforesaid sum exceeds about 50% of the lower discriminator setting of the aforesaid differential discriminator for defining the specific energy range of interest and is also less than the upper discriminator setting thereof.

7. The scintillation camera of claim 3 further comprising a plurality of preliminary differential discriminator means having different upper and lower discriminator levels which delineate energy bands within which pulses are rejected by said plurality of preliminary differential discriminator means.

8. The scintillation camera of claim 1 wherein said means for increasing maximum pulse acceptance rate includes means for detecting the concurrent existence in the position computation circuitry of electrical pulses emanating from the detection of different quanta of radiation, and means for preventing the registration of locations in response to signals emanating from said different quanta of radiation.

9. The scintillation camera of claim 8 wherein there are provided integration circuit means for receiving and integrating the sum of pulses emanating from said photodetectors, integrator reset means for resetting said integration circuit means at a determinable interval of time subsequent to detection of the associated quanta of radiation by said scintillation crystal, whereby the output amplitude of said integration circuit means from pulses integrated in response to a single detected quanta of radiation decays at a predictable rate upon actuation of said integrator reset means, comparator circuit means for comparing the output amplitude of said integration circuit means with an acceptable amplitude level related to the aforesaid predictable decay rate, and pulse rejection means for discarding pulses present in said position computation circuitry when the output amplitude of said integration circuit exceeds the aforesaid acceptable amplitude level.

10. The scintillation camera of claim 1 further comprising a DC coupled photodetector amplifier associated with each photodetector and wherein each photodetector has an anode operated at ground potential, and a photocathode connected to a negative high voltage source.

11. The scintillation camera of claim 1 wherein said specific energy range of interest is defined by a differential discriminator circuit having a median energy marker having upper and lower discriminators, controlled by a manually adjustable midrange energy selector for selecting a median energy setting, and wherein there is provided an adjustable window width selector which adjusts said upper and lower discriminators to levels which are respectively above and below said median energy marker by equal percentages of said median energy marker measured with respect to a base reference, and automatic feedback adjustment circuitry for maintaining said median energy marker at said median energy setting and for maintaining said median energy marker and said upper and lower discriminators in the foregoing prescribed relationship.

12. The scintillation camera of claim 11 wherein said median energy marker is comprised of an integration signal circuit carrying the integrated output of the aforesaid electrical pulses produced in response to a quanta of radiation connected in opposed polarity with a midrange energy selector circuit to an input of a comparative output amplifier means having another input from ground, said upper and lower discriminators are comprised of a proportional amplifier circuit with inputs derived from said midrange energy selector and from said window width selector and having dual outputs, one of which is connected to a unity gain inverting amplifier system to produce upper and lower discriminator levels, wherein outputs from said median energy marker are connected as inputs to separate differential amplifiers in respective opposition to said upper and lower discriminator levels and to said comparative output amplifier means as aforesaid, and said comparative output amplifier means is connected to an automatic gain adjustment circuit connected in feedback relationship to said median energy marker.

13. In a scintillation camera having a rated capacity for processing of detected radioactive events and including an array of photodetectors viewing overlapping portions of a scintillation crystal and producing electrical pulses in response to quanta of radiation impinging upon said scintillation crystal, which pulses are processed by position computation circuitry to register the relative locations of quanta of radiation detected by said crystal, the improvement wherein said position computation circuitry includes buffer storage means having a plurality of stages, each stage adapted to sequentially accommodate pulses derived from said photodetectors in response to specific detected quanta of radiation for periods of time during which the rate of detection of radioactive events momentarily exceeds the aforesaid rated capacity due to statistical fluctuations in the rate at which pulses are received for processing.

14. In a scintillation camera employing an array of photodetectors viewing overlapping portions of a scintillation crystal and producing electrical pulses in response to quanta of radiation impinging upon said scintillation crystal, which pulses are processed by position computation circuitry to register the relative locations of quanta of radiation detected by said crystal, and wherein said position computation circuitry includes pulse discrimination means operative to accept and reject pulses on the basis of amplitude measurements subsequent to pulse peaking, the improvement wherein said pulse amplitude discrimination means comprises means for preliminary pulse rejection and provisional pulse acceptance upon the basis of amplitude measurements prior to pulse peaking.

* * * * *